United States Patent [19]
Kaplitt et al.

[11] Patent Number: 6,162,796
[45] Date of Patent: Dec. 19, 2000

[54] METHOD FOR TRANSFERRING GENES TO THE HEART USING AAV VECTORS

[75] Inventors: Michael G. Kaplitt, New York; Martin J. Kaplitt, Floral Park, both of N.Y.; Edward B. Diethrich, Paradise Valley, Ariz.

[73] Assignee: The Rockefeller University, New York, N.Y.

[21] Appl. No.: 08/534,351

[22] Filed: Sep. 27, 1995

[51] Int. Cl.$^7$ .................................................... A61K 31/70
[52] U.S. Cl. ........................... 514/44; 435/455; 435/456; 435/325; 435/320.1
[58] Field of Search ................................ 435/320.1, 69.1, 435/172.3, 455, 456, 325; 424/93.1, 93.2, 93.6; 514/44; 536/23.1

[56] References Cited

U.S. PATENT DOCUMENTS

| | | | |
|---|---|---|---|
| 5,139,941 | 8/1992 | Muzyczka et al. | 435/172.3 |
| 5,252,479 | 10/1993 | Srivastava | 435/235.1 |
| 5,580,766 | 12/1996 | Mason et al. | 435/172.1 |
| 5,797,870 | 8/1998 | March et al. | 604/49 |

FOREIGN PATENT DOCUMENTS

| | | |
|---|---|---|
| WO 94/13788 | 6/1994 | WIPO . |
| WO 95/13392 | 5/1995 | WIPO . |
| WO 96/12681 | 5/1995 | WIPO . |
| WO 95/14771 | 6/1995 | WIPO . |
| WO 95/20671 | 8/1995 | WIPO . |
| WO 96/26742 | 9/1996 | WIPO . |

OTHER PUBLICATIONS

Marshall, E. Science. vol. 269, pp. 1050–1055, Aug. 25, 1995.
Crystal, R. Science, vol. 270, pp. 404–410, 1995.
Jolly, D. Cancer Gene Therapy. vol. 1, No. 1, pp. 51–64, 1994.
Orkin et al. NIH Report, Dec. 5, 1995.
Verma et al. Nature. vol. 389, pp. 239–242, Sep. 18, 1997.
Editorial. Nature Biotechnology, vol. 15, Sep. 1997.
Gura, T. Science. vol. 270, pp. 575–577, Oct. 27, 1995.
Roush, W. Science. vol. 276, pp. 1192–1193, May 23, 1997.
Gyurko et al. (1995) FASEB J. 9:A330.
Kaplitt et al. (1995) In: Viral Vectors. Chpt. 12:1–18, Academic Press, NY.
Kourtis et al. (1995) Modern Pathol. 8:33A.
Barr et al. (1994) Gene Therapy 1:51–8.
Duboc et al. (1994) Circulation 90:I–517 (No. 2784).
French et al. (1994) Circulation 90:I–517 (No. 2785).
Gnatenko et al. (1994) Blood 84:Abst.2949.
Guzman et al. (1994) Proc. Natl. Acad. Sci. USA 91:10732–6.
Kaplitt et al. (1994) Nature Genetics 8:148–54.
Nabel et al. (1994) Cardiovascular Res. 28:445–55.
Russell et al. (1994) Proc. Natl. Acad. Sci. USA 91:8915–9.
Sawa et al. (1994) Circulation 90:I–46 (No. 0239).
Flotte et al. (1993) J. Biol. Chem. 268:3781–90.
Flotte et al. (1993)Proc. Natl. Acad. Sci. USA 90:10613–7.
Flotte et al. (1992) Am. J. Respir. Cell. Mol. Biol. 7:349–56.
March et al. (1992) Eur. Heart J. 13:218.
Muro–Cacho et al. (1992) J. Immunoother. 11:231–7.
Nahreini et al. (1992) Gene 119:265–72.
Walsh et al. (1992) Proc. Natl. Acad. Sci. USA 89:7257–61.
Samulski et al. (1989) J. Virol. 63:3822–8.
McLaughlin et al. (1988) J. Virol. 62:1963–73.
Vastava et al. (1983) J. Virol. 45:555–64.

*Primary Examiner*—Remy Yucel
*Attorney, Agent, or Firm*—Klauber & Jackson

[57] ABSTRACT

The invention relates to the use of adeno-associated virus vectors for the transfer of genes to the heart and vasculature. The vector preferably contains a gene encoding a protein which improves heart and vascular function during heart failure. In a specific embodiment, the vector is introduced into the heart and vasculature via a catheter, with the aid of fluoroscopy. The method and vectors for use therein provide for safe and stable gene expression of the transferred genes.

36 Claims, 6 Drawing Sheets

METHOD FOR TRANSFERRING GENES TO THE HEART USING AAV VECTORS

TECHNICAL FIELD OF THE INVENTION

The present invention relates generally to methods for transferring genes into the heart and blood vessels. More specifically, the invention relates to methods for transferring genes into the mammalian heart and blood vessels using adeno-associated virus (AAV) vectors.

BACKGROUND OF THE INVENTION

The ability to deliver genes to the heart and blood vessels, and to manipulate their expression, may make possible the treatment of numerous cardiac disorders. Unfortunately, gene transfer into the heart and blood vessels presents several problems including the relative inaccessibility of the heart tissue, and the fact that cells of the heart are non-dividing, terminally differentiated cells. The standard approach for somatic cell gene transfer, i.e., that of retroviral vectors, is not feasible for the heart, as retrovirally mediated gene transfer requires at least one cell division for integration and expression.

Thus, non-retroviral vectors and non-viral methods, such as the direct injection of "naked" plasmid DNA into the heart, have therefore been used for gene transfer in the heart. The use of "naked" DNA is extremely inefficient for delivering genes to the heart, and expression of the genes transferred by such methods has been largely transient. In addition, naked DNA has only been successfully used to transduce heart cells in vivo after a direct needle injection into the heart muscle during a surgical procedure. This is impractical for widespread cardiac gene therapy and it only influences a small area of cardiac muscle.

A viral vector derived from hemagglutinating virus of Japan (HVJ), which was complexed with liposomes, has been used as an alternative to retroviral vectors and the direct injection of naked DNA (Sawa et al (1994) *Circulation* 90:I-46, Abstract 0239). However, this system was used in isolated hearts which were to be later transplanted, and was thus only considered to possibly provide new therapy for heart transplantation.

Adenovirus vectors have also been used to transfer genes to the heart, but they have likewise only been applied by direct needle injection into the heart muscle (Duboc et al (1994) *Circulation* 90:I-517, Abstract 2784; French et al (1994) *Circulation* 90:I-517, Abstract 2785) or using a rat carotid balloon injury model, in which a solution containing the vector is actually incubated in a blood vessel (Guzman et al (1994) *Proc. Natl. Acad. Sci. USA* 91:10732–10736). Adenovirus vectors are more efficient at transferring genes into the adult heart than naked DNA, but their expression has likewise only been transient.

Moreover, although adenovirus vectors are designed such that they lack one or more essential viral genes (i.e., the adenovirus E1a immediate early gene) and are thus replication deficient, they retain numerous viral genes which yield expression of viral proteins in addition to the foreign gene of interest. Hence, as a result of the continued production of viral proteins within target cells, significant inflammation can develop. Such inflammation can be an important factor limiting longevity of foreign gene expression. Moreover, this inflammation can be damaging to healthy tissue, which is undesirable if these vectors are intended to protect healthy tissue which is already at risk, or alternatively, if the function of healthy tissue were to be augmented in order to replace the functions lost in nearby damaged tissue. In any event, even in the absence of inflammation, these viral gene products may also be directly toxic to recipient cells. Finally, stability of long-term expression of genes transferred by adenovirus vectors is currently unclear since there is no mechanism for specific viral integration in the genome of non-dividing host cells at high frequency.

Adeno-Associated Virus (AAV) is a defective parvovirus whose genome is encapsidated as a single-stranded DNA molecule. Strands of plus and minus polarity are both packaged, but in separate virus particles. A productive infection requires co-infection by a non-AAV helper virus such as adenovirus or herpes virus, which provides proteins necessary for AAV replication and packaging. In the AAV vector system, 96% of the parental genome has been deleted such that only the terminal repeats remain, containing only recognition signals for DNA replication and packaging. AAV structural proteins are provided in trans by co-transfection with a helper plasmid containing the missing AAV genes but lacking replication/packaging signals.

Although AAV can replicate under special circumstances in the absence of a helper virus, efficient replication requires coinfection with a helper virus of the herpesvirus or adenovirus family. In the absence of the helper virus, AAV establishes a latent infection in which the viral genome exists as an integrated provirus in the host cell. No AAV gene expression is required to establish a latent infection. The integration of the virus is site-specific (chromosome 19). Overall, virus integration appears to have no apparent effect on cell growth or morphology. See Samulski, *Curr. Op. Gen. Devel.* 3:74–80 (1993). If a latently infected cell line is later superinfected with a suitable helper virus, the AAV provirus is excised and the virus enters the "productive" phase of its life cycle. However, it has been reported that certain AAV-derived transducing vectors are not rescued by adenovirus superinfection.

AAV has been isolated as a nonpathogenic coinfecting agent from fecal, ocular and respiratory specimens during acute adenovirus infections, but not during other illnesses. Although AAV is a human virus, its host range for lytic growth is unusually broad. Latent AAV infections have been identified in both human and nonhuman cells. Cell lines from virtually every mammalian species tested (including a variety of human, simian, canine, bovine and rodent cell lines) can be productively infected with AAV, provided an appropriate helper virus is used (e.g., canine adenovirus in canine cells). Despite this, no disease has been associated with AAV in either human or other animal populations, unlike both HSV and adenovirus.

The genome of AAV-2 is 4,675 bases in length and is flanked by inverted terminal repeat sequences of 145 bases each. These repeats are believed to act as origins for DNA replication. There are two major open reading frames. The left frame encodes at least four non-structural proteins (the Rep group). There are two promoters P5 and P19, which control expression of these proteins. As a result of differential splicing, the P5 promoter directs production of proteins Rep 78 and Rep 68, and the P19 promoter, Rep 52 and Rep 40. The Rep proteins are believed to be involved in viral DNA replication, trans-activation of transcription from the viral promoters, and repression of heterologous enhancers and promoters. The right ORF, controlled by the P40 promoter, encodes the capsid proteins Vp1 (91 kDa), Vp2 (72 kDa) and Vp3 (60 kDa). Vp3 comprises 80% of the virion structure, while Vp1 and Vp2 are minor components. There is a polyadenylation site at map unit 95. For the complete sequence of the AAV-2 genome, see Vastava et al (1983) *J. Virol.* 45:555–64.

McLaughlin et al (1988) *J. Virol.* 62:1963–73 prepared two AAV vectors: dl 52–91, which retains the AAV rep genes, and dl 3–94, in which all of the AAV coding sequences have been deleted. It does, however, retain the two 145 base terminal repeats, and an additional 139 bases which contain the AAV polyadenylation signal. Restriction sites were introduced on either side of the signal. A foreign gene, encoding neomycin resistance, was inserted into both vectors. Viral stocks were prepared by complementation with a recombinant AAV genome, which supplied the missing AAV gene products in trans but was itself too large to be packaged. Unfortunately, the virus stocks were contaminated with wild type AAV (10% in the case of dl 3–94) presumably as a result of homologous recombination between the defective and the complementing virus.

Samulski et al (1989) *J. Virol.* 63:3822–28 developed a method of producing recombinant AAV stocks without detectable wild-type helper AAV. Their AAV vector retained only the terminal 191 bases of the AAV chromosome. In the helper AAV, the terminal 191 bases of the AAV chromosome were replaced with adenovirus terminal sequences. Since sequence homology between the vector and the helper AAV was thus essentially eliminated, no detectable wild-type AAV was generated by homologous recombination. Moreover, the helper DNA itself was not replicated and encapsidated because the AAV termini are required for this process. Thus, in the AAV system, unlike the HSV system, helper virus could be completely eliminated leaving a helper-free AAV vector stock.

Muro-Cacho et al (1992) *J. Immunother.* 11:231–237 have used AAV-based vectors for gene transfer into both T- and B-lymphocytes. Walsh et al (1992) *Proc. Nat. Acad. Sci. (USA)* 89:7257–61 used an AAV vector to introduce a human gamma globulin gene into human erythroleukemia cells; the gene was expressed. Flotte et al (1993) *J. Biol. Chem.* 268:3781–90 delivered the cystic fibrosis transmembrane conductance regulator gene to airway epithelial cells by means of an AAV vector. See also Flotte et al (1992) *Am. J. Respir. Cell. Mol. Biol.* 7:349–56; Flotte et al (1993) *Proc. Nat. Acad. Sci. (USA)* 90:10613–17; Kaplitt et al (1994) *Nature Genetics* 8:148–154).

In view of the aforementioned insufficiencies associated with prior art methods of delivering foreign genes to the heart and blood vessels, it is apparent that there exists a need for such a method which provides safe and stable gene expression, preferably without invasive procedures.

SUMMARY OF THE INVENTION

In accordance with the present invention, a method and the vectors for use therein are provided for the efficient transfer of genes to cells of the heart and blood vessels, using an AAV vector. The method results in the safe and stable expression of genes so transferred.

In its broadest aspect, the present invention extends to methods of transferring genes to the heart and blood vessels using AAV vectors. Such methods include delivery of the AAV vector via direct injection of the heart tissue and/or coronary arteries, as well as delivery via a catheter inserted into a peripheral artery.

In specific embodiments, the AAV vector expresses a gene which allows the heart to function better during failure and/or promote activity of heart muscle. Such genes may encode an enzyme including, but not limited to tyrosine hydroxylase, aromatic acid decarboxylase and the adenosine A1 receptor. Likewise, DNA encoding factors which are involved in blot clotting or its inhibition, such as, for example, tissue plasminogen activator, streptokinase or urokinase may be included in the AAV vector. In a further embodiment, the AAV vector may include DNA encoding a growth factor such as platelet derived growth factor (PDGF), fibroblast growth factor (FGF), transforming growth factor (TGF), insulin-like growth factor (IGF), epidermal growth factor (EGF) and the like. In a still further aspect, the present invention extends to AAV vectors which contain DNA encoding proteins involved in cholesterol metabolism, circulation, and accumulation, such as, for instance, the low density lipoprotein receptor (LDLR). In yet other embodiments, the AAV vector may contain DNA encoding a gene encoding a protein involved in angiogenesis, or a protein or peptide involved in the control of blood pressure, such as angiotensin, renin and the like. In another embodiment, the AAV vector may include a gene encoding protective factors such as HSP-70, which is a heat-shock protein that has a protective effect on cells which are under stress, or superoxide dismutase or catalase, which protect cells from free-radical damage. In yet another embodiment, the AAV vector may include a gene encoding a protein which may render cells susceptible to a particular drug, such as thymidine kinase.

The invention also extends to the AAV vectors containing the genes described above.

In another aspect, the invention relates to an AAV vector comprising a gene, which when expressed, encodes a mRNA which acts as an antisense RNA and inhibits expression of endogenous proteins in the cell. The invention also relates to methods of delivering such antisense vectors.

The use of AAV vectors for transferring genes to the heart has particular advantages over other methods. In particular, because AAV coat proteins are structurally distinct from those of the helper adenovirus, contaminating adenovirus particles can be completely removed from the AAV isolate. Thus, the AAV vector is unique among current DNA viral vectors, as it contains only the gene of interest with no viral genes, and it is completely free of contaminating helper virus. Therefore, a principal source of pathogenicity is eliminated, rendering this system particularly suited to human gene therapy.

Furthermore, studies show that AAV vectors integrate directly into host chromosomes (Walsh et al (1992) *Proc. Natl. Acad. Sci. USA* 89:7257–7261; Russell et al (1994) *Proc. Natl. Acad. Sci. USA* 91:8915–8919). Using Southern blots, these studies showed that cells stably transduced with AAV vectors contain genomes integrated within the host chromosome, in single-copy fashion. Moreover, the vector DNA persists within transduced cells. This supports the idea that AAV vectors provide a safe means of establishing long-term expression of DNA, making this system particularly well suited for human gene therapy.

The ability of AAV to transfer genes into heart muscle or vascular endothelial cells, resulting in long-term expression is unexpected in light of the lack of previous reports, to the inventor's knowledge, that AAV naturally infects heart muscle. Since the receptor for AAV is presently unknown, it was not clear whether adult myocardial cells would be capable of infection by AAV. In fact, the present inventors have demonstrated that AAV vectors can yield long-term expression not observed with other systems. Moreover, the present vector system has the advantage that the vector itself does not induce the expression of an endogenous cellular heat shock protein (HSP) of 70 kD in terminally differentiated cells. This protein is commonly used as a marker of cell stress or damage, and the lack of induction indicates that AAV vectors safely transduce terminally differentiated cells. In contrast, adenovirus vectors do induce expression of the 70 kD heat shock protein, indicating that even in the absence of an immune system, even non-replicating adenovirus vectors induce stress upon cells.

As noted above, previous methods of transferring genes into the heart have involved direct injection into the cardiac muscle. Direct injection has limited practical value in the gene therapy of cardiac disease, however, since direct injection (1) does not allow for widespread gene delivery to a large area; and (2) can only be performed efficiently as an adjunct to open heart surgery. In contrast, a particular embodiment of the present invention provides a method of percutaneously inserting a catheter into the coronary arteries with the aid of fluoroscopy, to allow injection of fluid into the coronary arteries. Such a method has only been used in the past to deliver contrast dyes in order to visualize coronary artery anatomy or to deliver drugs such as streptokinase which act within the lumen of the blood vessel.

Moreover, the present invention results in gene transfer and expression to a wide area of heart muscle. This is in contrast to previous reports that adenovirus gene transfer and expression is limited to the blood vessel walls within the heart and transfer to heart muscle cells is virtually absent. The ability of the present invention to transfer genes to heart muscle cells is further surprising in light of the high rate of blood flow through the coronary arteries and constant motion of the heart, which might conceivably interfere with the interaction of the viral vector with its receptor. One advantage of the AAV vector over the vectors of the prior art in this regard is the fact that AAV is from smaller than adenovirus or herpesvirus vectors, and this may promote transit across capillaries into the muscle itself.

Accordingly, it is a principal object of the present invention to provide an AAV-derived vector which includes AAV sequences representing essentially only the replication and packaging signals of AAV; and a gene encoding a protein which, when expressed in cardiac muscle cells or vascular endothelial cells, improves cardiac or vascular function.

A further object of the invention is to provide a method of delivering DNA which is exogenous to both adeno-associated virus and to a mammalian heart or circulatory system target cell which includes providing an adeno-associated virus-derived vector which has been modified to include the exogenous DNA and causing the vector to transduce the cell.

A still further object of the invention is to provide a method of preventing, treating or ameliorating a genetically determined, predisposed, or affected disorder of the heart or vasculature which includes delivering exogenous DNA to cells of the heart or vasculature, wherein the exogenous DNA is chosen so that the delivery will prevent, treat or ameliorate the genetically determined, predisposed, or affected disorder of the heart or vasculature.

Other objects and advantages will become apparent to those skilled in the art from a review of the ensuing description which proceeds with reference to the following illustrative drawings.

DETAILED DESCRIPTION

Figure 1:
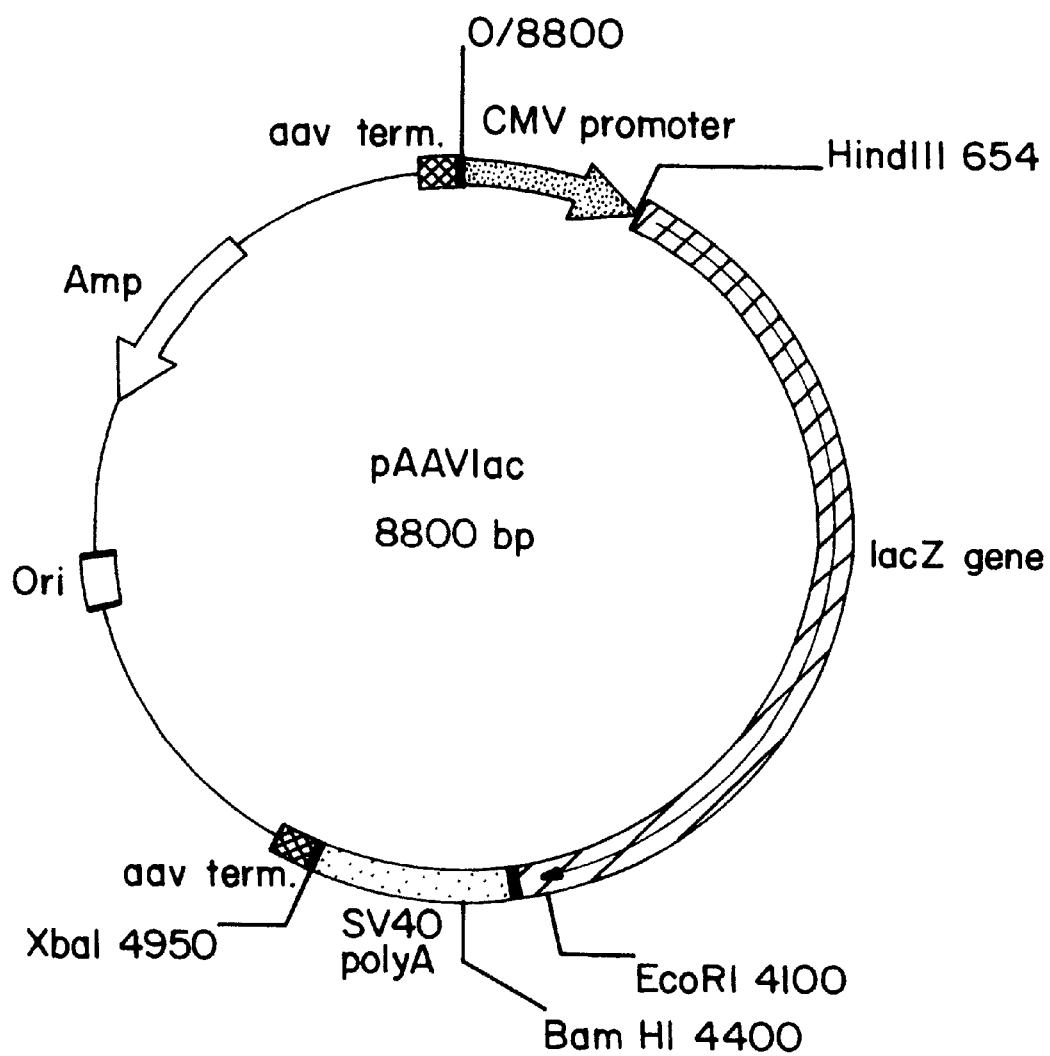
FIG. 1 is a schematic drawing of plasmid pAAVlac.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The proteins encoded by the present AAV vectors should be considered as including any variants not specifically listed, and may be used herein interchangeably, and as used throughout the present application and claims refer to proteinaceous material including single or multiple proteins, and extends to those proteins having the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Such proteins are intended to include within their scope proteins specifically recited herein as well as all substantially homologous analogs and allelic variations.

The amino acid residues of which the proteins described herein are comprised, are preferably in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |

-continued

TABLE OF CORRESPONDENCE

| SYMBOL | | |
|---|---|---|
| 1-Letter | 3-Letter | AMINO ACID |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences where initiation of DNA replication occurs.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" or "transduced" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In its primary aspect, the present invention concerns the use of an AAV-derived vector for delivering a gene to cells of the heart and vasculature.

In a particular embodiment, the present invention relates to genes which encode proteins which improve heart and vascular function, particularly during heart failure.

In another embodiment, in instances where it is desired to reduce or inhibit the gene activity resulting from a particular stimulus or factor, an AAV-derived vector which encodes an antisense RNA, which binds to the mRNA of the endogenous gene is introduced to block the activity of the target gene product. Correspondingly, instances where insufficient gene activation is taking place could be remedied by the introduction of additional quantities of the gene of interest or its chemical or pharmaceutical cognates, analogs, fragments and the like.

As used herein, "pg" means picogram, "ng" means nanogram, "ug" or "μg" mean microgram, "mg" means milligram, "ul" or "μl" mean microliter, "ml" means milliliter, "l" means liter.

Another feature of this invention is the expression of the DNA sequences encoding proteins or peptides which have an effect on cardiac or vascular function. As is well known in the art, DNA sequences may be expressed by operatively linking them to an expression control sequence. Such operative linking of a DNA sequence of this invention to an expression control sequence, of course, includes, if not already part of the DNA sequence, the provision of an initiation codon, ATG, in the correct reading frame upstream of the DNA sequence.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In selecting an expression control sequence, a variety of factors will normally be considered. These include, for example, the relative strength of the system, its controllability, and its compatibility with the particular DNA sequence or gene to be expressed, particularly as regards potential secondary structures. Considering these and other factors a person skilled in the art will be able to construct a variety of vector/expression control sequence combinations that will express the DNA sequences of this invention.

It is further intended that analogs may be prepared from nucleotide sequences encoding the proteins having effects on cardiac and vascular function within the scope of the present invention. Analogs, such as muteins, can be produced by standard site-directed mutagenesis of the genes' coding sequences. Analogs exhibiting activity toward cardiac or vascular function such as small molecules, whether functioning as promoters or inhibitors, may be identified by known in vivo and/or in vitro assays.

As mentioned above, a DNA sequence encoding the gene can be prepared synthetically rather than cloned. The DNA sequence can be designed with the appropriate codons for the desired amino acid sequence. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express such analogs or "muteins". Alternatively, DNA-encoding muteins can be made by site-directed mutagenesis of native genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

The present invention extends to the preparation of antisense nucleotides and ribozymes that may be used to interfere with the expression of the target gene at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for the target proteins and their ligands.

The present invention also relates to a variety of diagnostic applications, including methods for imaging the heart and vasculature, as well as methods of tracking blood flow and the ultimate fate of the AAV which is introduced into the blood vessel. By using a reporter gene either alone, or in combination with a gene which is directed at altering a function of the heart or vasculature, one can detect using the proper imaging system, the location of cells which have been efficiently transduced with the vector. As such, this provides insight into blood flow and altered morphology in the heart and vasculature. Such reporter genes may include, for example, the luciferase gene, the β-galactosidase gene, or any other gene, the presence of which may be detected. As will be evident from the type of label used, some labels will require that tissue be excised from the subject in order to detect the presence of the gene product. Thus, preferred methods include labels which may be detected without such an invasive procedure. This may include, for example, using the HSV thymidine kinase gene as a marker and a radioactive analog of ganciclovir or deoxyuridine as a substitute.

The presence of the transduced gene product in cells can also be ascertained by the usual immunological procedures applicable to such determinations. A number of useful procedures are known. Such procedures which are especially useful utilize either the innate characteristics of the gene product itself which is detectable, or involve the addition of a ligand or antibody specific for the gene product which has been labeled with a detectable label, antibody $Ab_1$ labeled with a detectable label, or antibody $Ab_2$ labeled with a detectable label. The procedures may be summarized by the following equations wherein the asterisk indicates that the particle is labeled, and "GP" stands for the gene product:

A. $GP^* + Ab_1 = GP^*Ab_1$

B. $GP + Ab^* = GPAb_1^*$

C. $GP + Ab_1 + Ab_2^* = GPAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the gene product forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-GP antibody, and $Ab_2$ will be referred to as a secondary or anti-$Ab_1$ antibody.

The labels most commonly employed for these studies are radioactive elements, enzymes, chemicals which fluoresce when exposed to ultraviolet light, luciferase and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The gene product or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Likewise, Southern blots and PCR may be used to identify the presence of the gene, while PCR, primer extension and Northern blots may be used to detect the mRNA. Such techniques are well known in the art, and protocols therefore set forth in Sambrook et al., supra.

Accordingly, a test kit may be prepared for the demonstration of the presence of a transduced gene, comprising:

(a) a predetermined amount of at least one labeled immunochemically reactive component obtained by the direct or indirect attachment of the gene product or a specific binding partner thereto, to a detectable label;

(b) other reagents; and (c) directions for use of said kit.

In accordance with the above, an assay system for screening potential drugs effective to modulate the activity of the gene product may be prepared. The prospective drug may be introduced into the subject, and the subject thereafter examined to observe any changes in the transcriptional activity of the cells, due either to the addition of the prospective drug alone, or due to the effect of added quantities of the known gene product.

The principles and procedures for gene transfer in vascular disease are reviewed in detail in Nabel et al (1994) *Cardiovascular Research* 28:445–455, which is hereby incorporated by reference in its entirety. Additionally, the use of AAV vectors to transfer genes to the mammalian nervous system is discussed in Kaplitt et al (1994) *Nature Genetics* 8:148–154 and Kaplitt and During (1995) "Transfer and Expression of Potentially Therapeutic Genes into the Mammalian Central Nervous System in Vivo Using Adeno-Associated Viral Vectors," in *Viral Vectors,* Academic Press, both of which are also hereby incorporated by reference in their entirety.

The following examples are presented in order to more fully illustrate the preferred embodiments of the invention. They should in no way be construed, however, as limiting the broad scope of the invention.

EXAMPLE

Figure 2A:
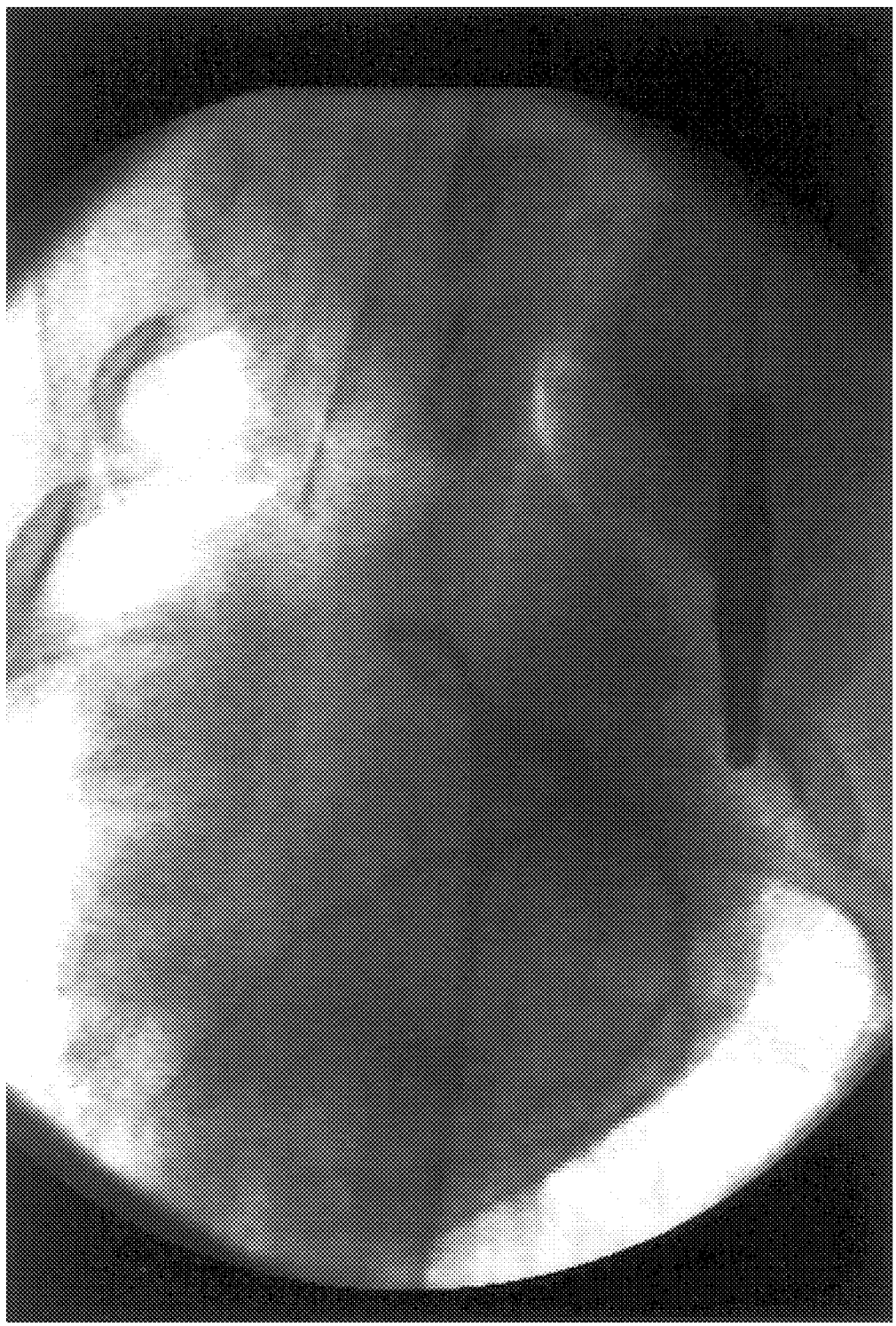
FIG. 2 is an angiogram of catheterized pig heart (1 of 3 replicates). The catheter which injected dye first, and then injected AAVlac into the pig heart can be seen, as well as the circumflex coronary artery filled with dye. The dye was flushed with saline, then AAVlac (1 ml of $10^7$ vector/ml) was injected.
Figure 2B:
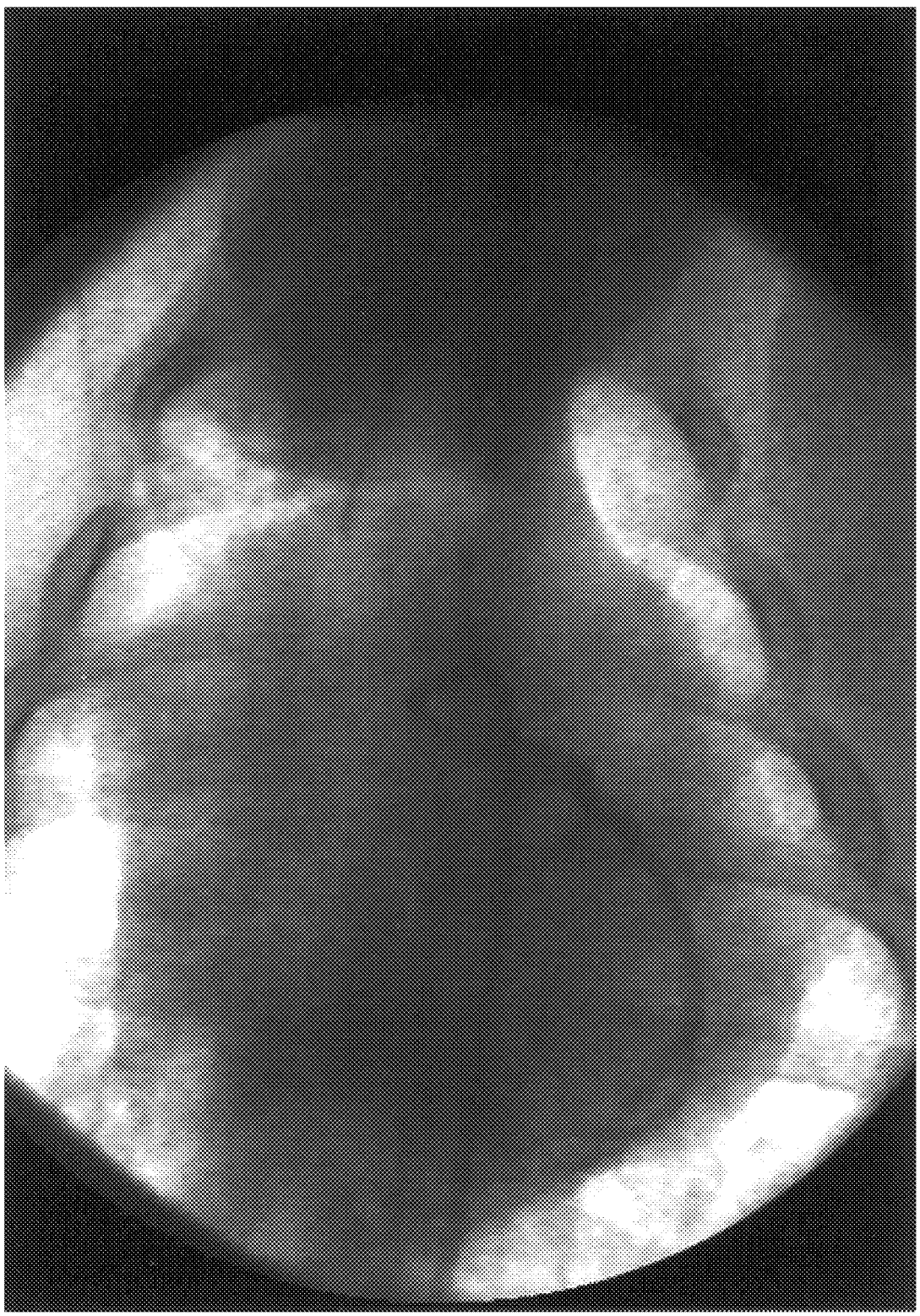
Figure 3A:
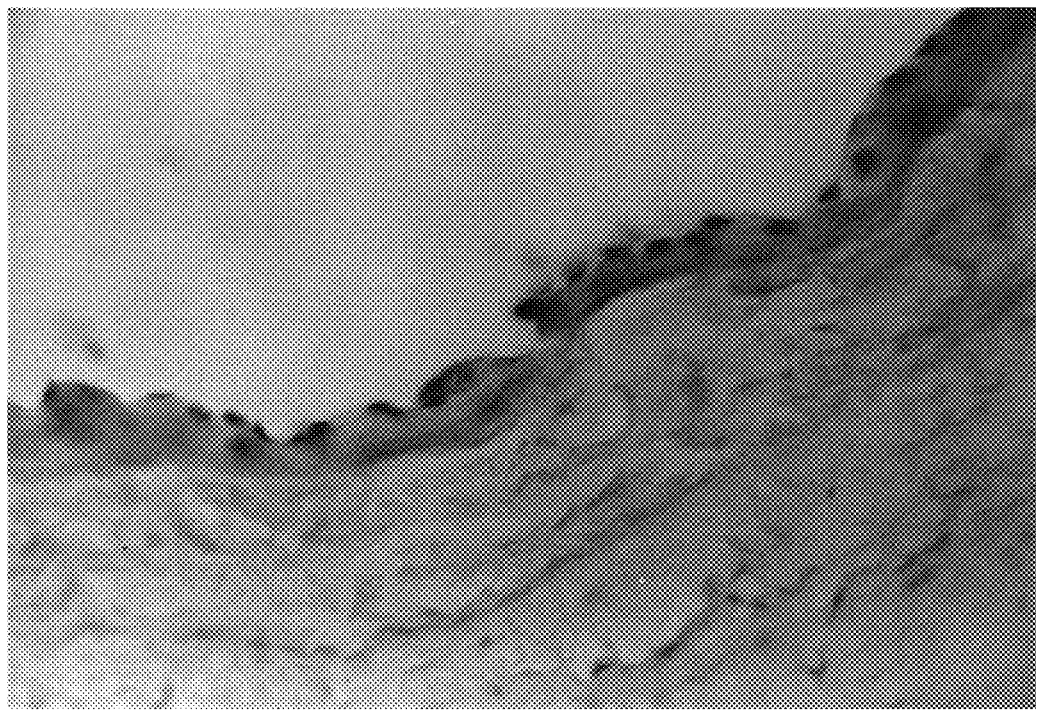
FIG. 3 shows β-gal positive cells in pig heart.
Figure 3B:
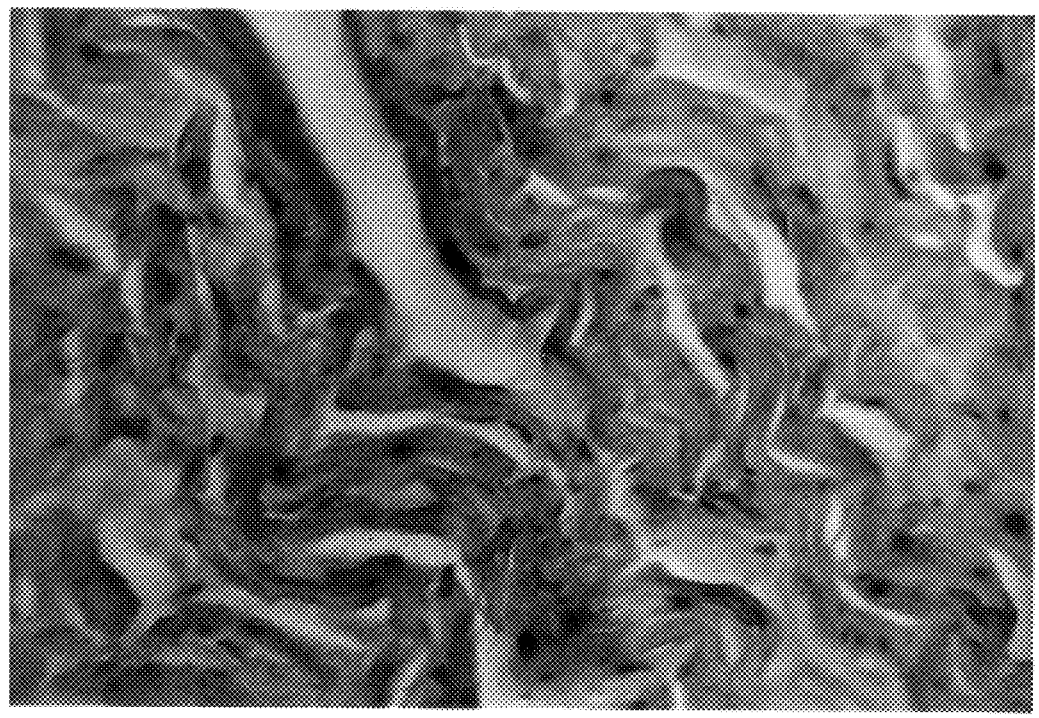
Figure 4:
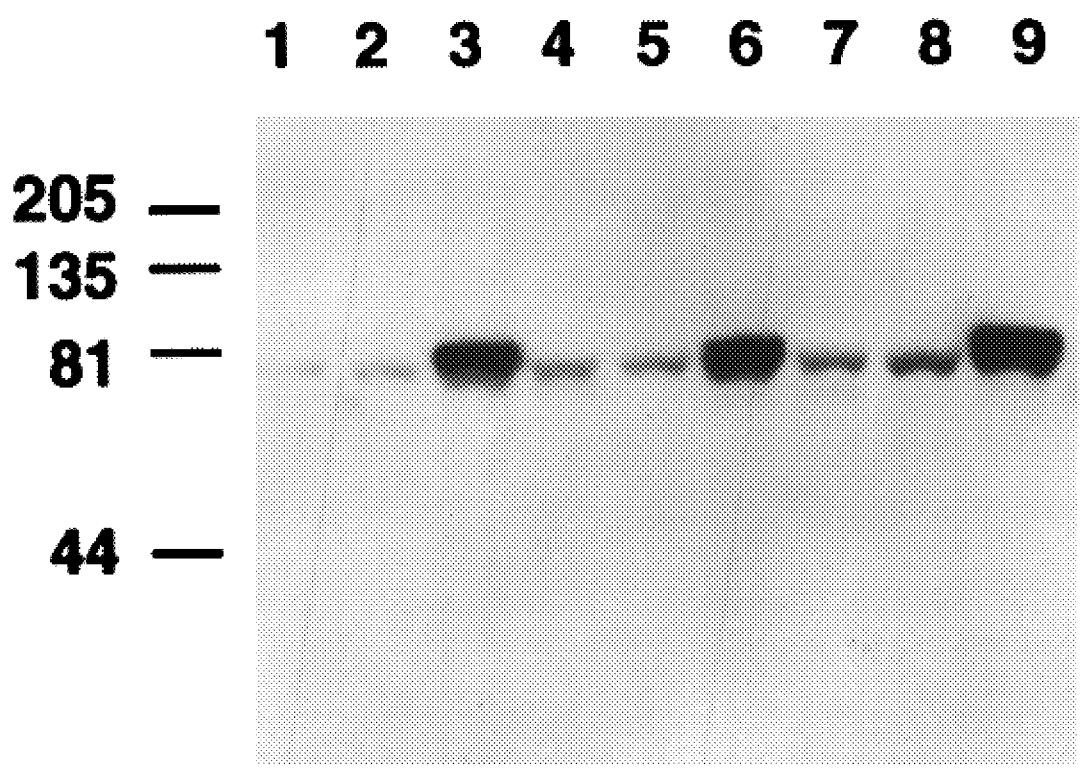
FIG. 4 is a Western blot of AAV-Hsp70. Lanes 1, 2, 4, 5, 7, and 8 are negative (AAVlac), while lanes 3, 6 and 9 are positive (AAV-Hsp70).
Figure 5:
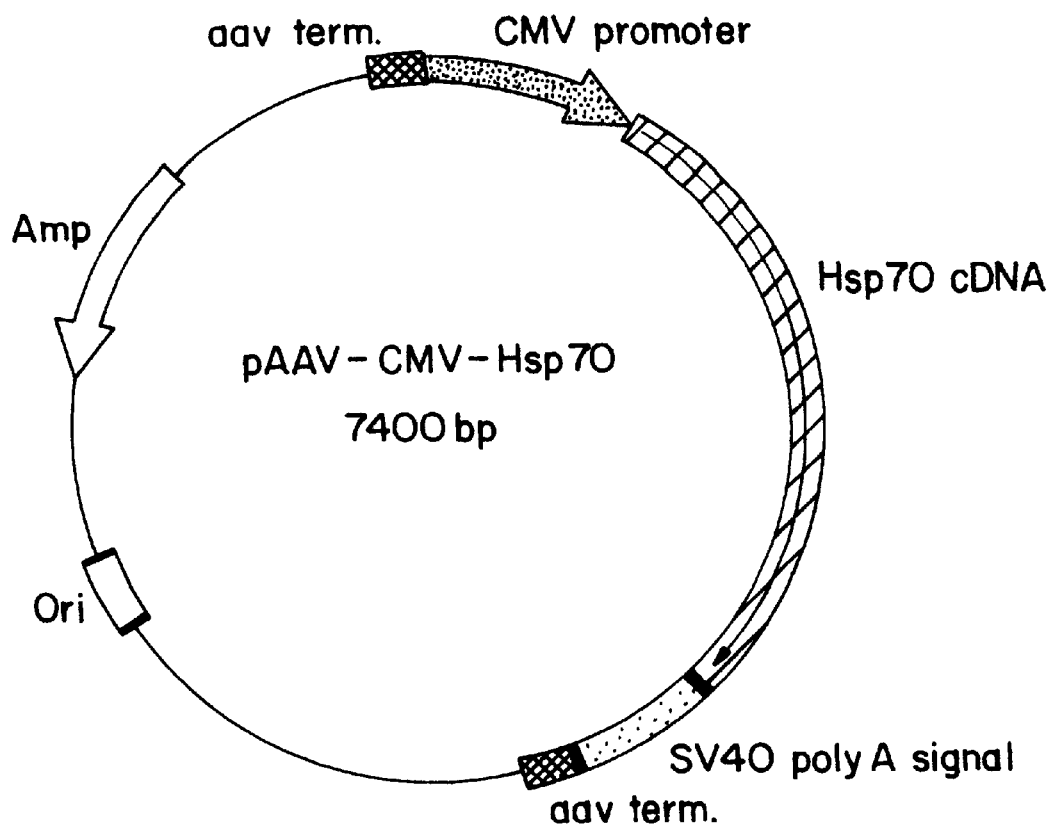
FIG. 5 is a schematic drawing of pAAV-CMV-Hsp70.

Pigs were used for transfer of AAV constructs to the blood vessels and heart. Access to the arterial system was obtained via cutdown to the right femoral artery. An 8 Fr. sheath was placed in the artery via the Seldinger technique. Systemic heparin, 2–3000 units, was administered. The left main coronary artery was engaged using an 8 Fr. hockey stick guide catheter. A Medtronic transfer catheter was advanced over a 0.014 inch Hi-Torque floppy exchange length guidewire, ACS. The guidewire was placed in the mid-circumflex coronary artery. The transfer catheter was advanced over the guidewire to the mid-circumflex coronary artery. The guidewire was then removed. Injection of isovue-370 was used to verify positioning of both the guide catheter and the transfer catheter. Virus was then injected using 1–3 cc aliquots. A saline flush was then used to clear residual material from the transfer catheter. All catheters were then removed and the sheath was also removed. The femoral artery was then ligated and the skin closed using interrupted sutures. Results are shown in FIGS. 2 and 3.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of delivering DNA which is exogenous to both adeno-associated virus (AAV) and a target cell, comprising delivering an adeno-associated virus vector to said target cell; wherein the adeno-associated virus vector comprises:

a. AAV sequences consisting essentially of the replication and packaging signals of AAV; and b. the exogenous DNA; wherein the exogenous DNA comprises an expressible gene encoding a protein which is expressed in said target cell using the vector; and wherein said target cell is selected from the group consisting of a cardiac muscle cell and a vascular endothelial cell.

2. The method of claim 1, wherein the expressible gene encodes an enzyme.

3. The method of claim 2, wherein the enzyme is superoxide dismutase.

4. The method of claim 1, wherein the expressible gene encodes a protein having an activity on one or more components of blood.

5. The method of claim 4, wherein the protein is streptokinase, urokinase or tissue plasminogen activator.

6. The method of claim 1, wherein the expressible gene encodes a protein which is protective to cells under stress.

7. The method of claim 6, wherein the protein is a heat shock protein.

8. The method of claim 7, wherein the heat shock protein has an apparent molecular weight of approximately 70 kD.

9. The method of claim 1, wherein the expressible gene encodes a growth factor.

10. The method of claim 9, wherein the growth factor is platelet derived growth factor, fibroblast growth factor, epidermal growth factor, transforming growth factor or insulin-like growth factor.

11. The method of claim 1, wherein the expressible gene encodes a protein involved in cholesterol metabolism, circulation or accumulation.

12. The method of claim 11, wherein the protein is the low density lipoprotein receptor.

13. The method of claim 1, wherein the expressible gene encodes a protein which is involved in angiogenesis.

14. The method of claim 1, wherein the expressible gene encodes a polypeptide involved in controlling blood pressure.

15. The method of claim 14, wherein the protein is renin, angiotensin, or an enzyme involved in the activation of renin or angiotensin.

16. The method of claim 1, wherein the expressible gene is expressed in said target cell either constitutively or under regulatable conditions.

17. The method of claim 16, wherein the expressible gene encodes a messenger RNA which is antisense with respect to a messenger RNA transcribed from a gene endogenous to said cell.

18. The method of claim 16, wherein the expressible gene encodes an enzyme which reduces the level of free radicals.

19. The method of claim 16, wherein the expressible gene encodes thymidine kinase.

20. The method of claim 16, wherein the expressible gene comprises a coding sequence and a regulatory sequence operably linked to said coding sequence, whereby, when said regulatory sequence is activated, a messenger RNA transcript is transcribed from said coding sequence.

21. The method of claim 1, wherein the adeno-associated virus vector retains only the inverted terminal repeats of AAV.

22. The method of claim 1, wherein said target cell is a mammalian cell of a mammalian order selected from the group consisting of Primata, Rodenta, Carnivora and Arteriodactyla.

23. The method of claim 22, wherein said mammalian cell is a human cell.

24. The method of claim 1, wherein said target cell is a vascular endothelial cell.

25. A method of delivering an adeno-associated virus vector to a cell of a mammalian heart, comprising administering said vector via a catheter inserted into a peripheral artery and delivering said vector to said cell in vivo, wherein said vector transduces said cell.

26. The method of claim 25, wherein said vector comprises DNA which is exogenous to both the adeno-associated virus and to said cell of the mammalian heart.

27. The method of claim 26 wherein the exogenous DNA comprises an expressible gene and said gene is expressed in said cell of the mammalian heart either constitutively or under regulatable conditions.

28. The method of claim 27, wherein the expressible gene encodes a messenger RNA which is antisense with respect to a messenger RNA transcribed from a gene endogenous to said cell.

29. The method of claim 27, wherein the expressible gene encodes a growth factor.

30. The method of claim 27, wherein the expressible gene encodes an enzyme which reduces the level of free radicals.

31. The method of claim 27, wherein the expressible gene encodes thymidine kinase.

32. The method of claim 27, wherein said vector does not comprise any AAV gene in functional form.

33. The method of claim 27, wherein said vector retains only the inverted terminal repeats of AAV.

34. The method of claim 27, wherein the expressible gene comprises a coding sequence and a regulatory sequence operably linked to said coding sequence, whereby, when said regulatory sequence is activated, a messenger RNA transcript is transcribed from said coding sequence.

35. The method of claim 25, wherein said cell is a mammalian cell of a mammalian order selected from the group consisting of Primata, Rodenta, Carnivora and Arteriodactyla.

36. The method of claim 35, wherein said mammalian cell is a human cell.

* * * * *